(12) United States Patent
Chen et al.

(10) Patent No.: US 12,299,873 B2
(45) Date of Patent: May 13, 2025

(54) SYSTEMS AND METHODS FOR CONNECTING SEGMENTED STRUCTURES

(71) Applicant: Intuitive Surgical Operations, Inc., Sunnyvale, CA (US)

(72) Inventors: Shiyang Chen, Mountain View, CA (US); Pechin Chien Pau Lo, Santa Clara, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 763 days.

(21) Appl. No.: 17/435,833

(22) PCT Filed: Mar. 12, 2020

(86) PCT No.: PCT/US2020/022313
§ 371 (c)(1),
(2) Date: Sep. 2, 2021

(87) PCT Pub. No.: WO2020/186015
PCT Pub. Date: Sep. 17, 2020

(65) Prior Publication Data
US 2022/0156923 A1 May 19, 2022

Related U.S. Application Data

(60) Provisional application No. 62/817,300, filed on Mar. 12, 2019.

(51) Int. Cl.
*G06T 7/00* (2017.01)
*A61B 34/00* (2016.01)
(Continued)

(52) U.S. Cl.
CPC ............ *G06T 7/0012* (2013.01); *A61B 34/25* (2016.02); *A61B 90/37* (2016.02); *G06T 7/10* (2017.01);
(Continued)

(58) Field of Classification Search
CPC ......... G06T 7/0012; G06T 7/10; A61B 34/25; A61B 90/37
See application file for complete search history.

(56) References Cited

U.S. PATENT DOCUMENTS

2010/0310146 A1* 12/2010 Higgins .................. G06T 7/162
345/419
2013/0236076 A1* 9/2013 Averbuch .............. G06T 7/0012
382/131
(Continued)

FOREIGN PATENT DOCUMENTS

CN 109377458 A 2/2019

OTHER PUBLICATIONS

International Preliminary Report on Patentability for Application No. PCT/US2020/022313, mailed on Sep. 23, 2021, 11 pages.
(Continued)

*Primary Examiner* — David Bilodeau
(74) *Attorney, Agent, or Firm* — Haynes & Boone, LLP.

(57) ABSTRACT

A system comprises a display system and a control system communicatively coupled to the display system. The control system is configured to receive anatomic image data for an anatomic tree structure and generate an initial segmentation of the anatomic image data. The initial segmentation includes a trunk structure and a branched structure unconnected to the trunk structure. The control system is also configured to determine whether to connect the branched structure to the trunk structure based on an assessment of a shape of the branched structure and an assessment of a
(Continued)

relationship between the trunk structure and the branched structure.

17 Claims, 11 Drawing Sheets

(51) Int. Cl.
*A61B 90/00* (2016.01)
*G06T 7/10* (2017.01)
(52) U.S. Cl.
CPC .................. *G06T 2200/24* (2013.01); *G06T 2207/30061* (2013.01)

(56) References Cited

U.S. PATENT DOCUMENTS

| | | | |
|---|---|---|---|
| 2016/0070878 A1* | 3/2016 | Soper | ................ A61B 34/10 703/11 |
| 2017/0228868 A1 | 8/2017 | Song et al. | |
| 2017/0278243 A1* | 9/2017 | Kang | ..................... A61B 6/504 |
| 2018/0071027 A1* | 3/2018 | Taylor | .................. A61B 8/5223 |
| 2018/0235709 A1* | 8/2018 | Donhowe | ................. G06T 7/33 |
| 2020/0030044 A1* | 1/2020 | Wang | ................. G06F 3/04815 |
| 2022/0273180 A1* | 9/2022 | Lavi | ...................... G06T 7/0012 |

OTHER PUBLICATIONS

Graham M.W., et al., "Robust 3-D Airway Tree Segmentation for Image-guided Peripheral Bronchoscopy," IEEE Transactions on Medical Imaging, Apr. 2010, vol. 29 (4), pp. 982-997.

International Search Report and Written Opinion for Application No. PCT/US2020/022313, mailed Jul. 20, 2020, 19 pages.

Invitation to pay additional fee received from the International Search AuthorityforApplication No. PCT/US2020/022313, mailed May 28, 2020, 13 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

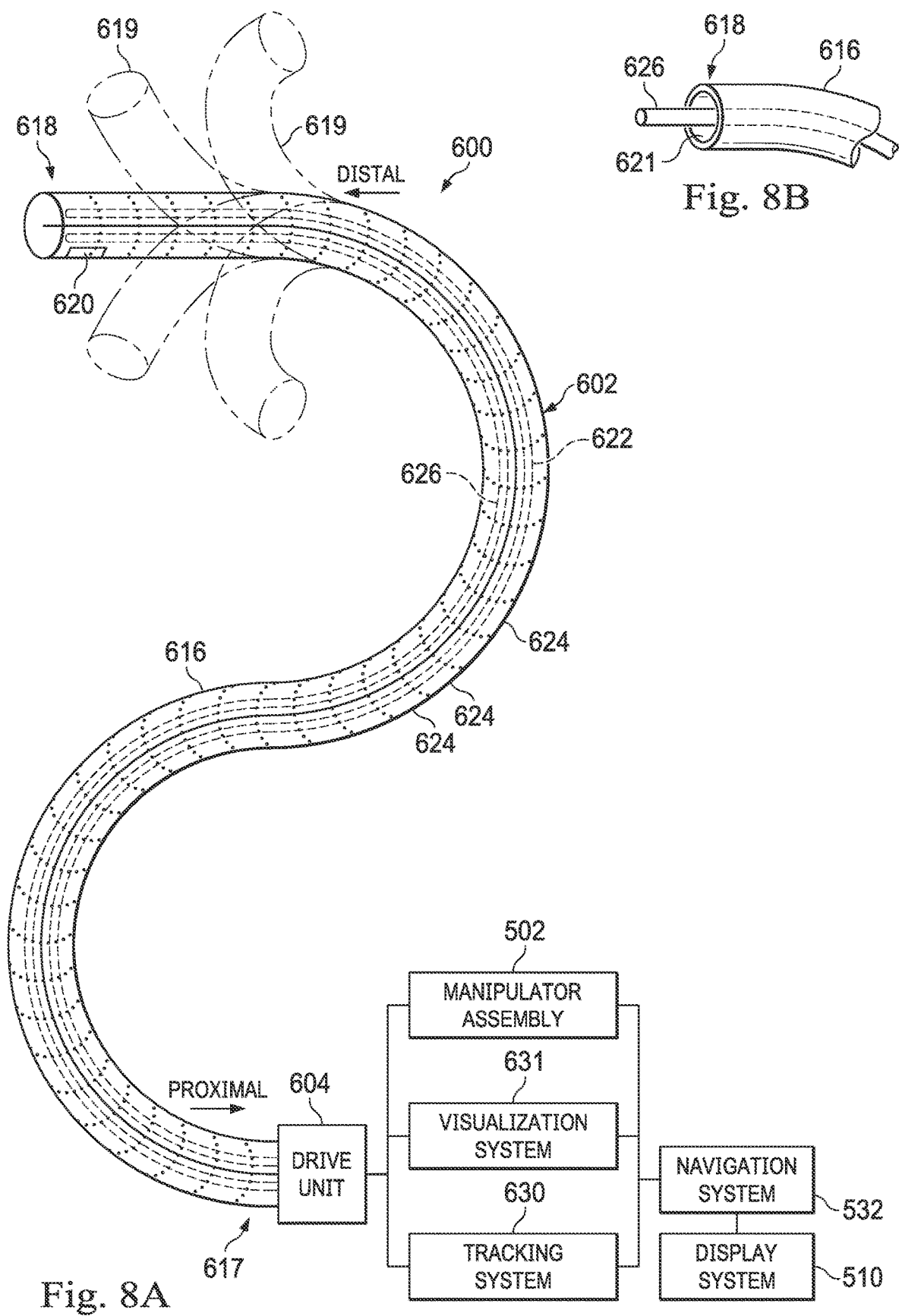

SYSTEMS AND METHODS FOR CONNECTING SEGMENTED STRUCTURES

CROSS-REFERENCE TO RELATED APPLICATIONS

This application is the U.S. national stage of International Application No. PCT/US2020/022313, filed Mar. 12, 2020, which designated the U.S. and claims priority to and the benefit of U.S. Provisional Application 62/817,300 filed Mar. 12, 2019, both of which are incorporated by reference herein in their entirety.

FIELD

The present disclosure is directed to systems and methods for generating images of anatomical tree structures.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert, minimally invasive medical tools to reach a target tissue location. Minimally invasive medical tools include instruments such as therapeutic, diagnostic, biopsy, and surgical instruments. Medical tools may be inserted into anatomic passageways and navigated toward a region of interest within a patient anatomy. Navigation may be assisted using images of the anatomic passageways. Improved systems and methods are needed to accurately perform image segmentation and generate anatomical tree structures that correspond to the patient's anatomy.

SUMMARY

Embodiments of the invention are best summarized by the claims that follow the description.

Consistent with some embodiments, a system is provided. The system includes a display system. The system further includes a control system communicatively coupled to the display system. The control system is configured to receive anatomic image data for an anatomic tree structure. The control system is further configured to generate an initial segmentation of the anatomic image data. The initial segmentation includes a trunk structure and a branched structure unconnected to the trunk structure. The control system is further configured to determine whether to connect the branched structure to the trunk structure based on an assessment of a shape of the branched structure and an assessment of a relationship between the trunk structure and the branched structure.

Consistent with other embodiments, a system is provided. The system includes a display system. The system further includes a control system communicatively coupled to the display system. The control system is configured to receive anatomic image data for an anatomic tree structure. The control system is further configured to generate an initial segmentation of the anatomic image data. The initial segmentation includes a trunk structure and a branched structure unconnected to the trunk structure. The control system is further configured to display the branched structure and the trunk structure on a display system. The branched structure is displayed with a visual characteristic different from the trunk structure. The control system is further configured to receive an indication of a user's intent to at least one of adding the branched structure to the trunk structure or removing the branched structure.

Consistent with other embodiments, a system is provided. The system includes a display system. The system further includes a control system communicatively coupled to the display system. The control system is configured to receive anatomic image data for an anatomic tree structure. The control system is further configured to generate an initial segmentation of the anatomic image data. The initial segmentation includes a trunk structure and a branched structure unconnected to the trunk structure. The control system is further configured to display the trunk structure on a display system. The control system is further configured to receive an indication of a user's intent to grow the initial segmentation into an indicated region adjacent to the trunk structure. The control system is further configured to display the branched structure if the branched structure is located in the indicated region adjacent to the trunk structure.

Consistent with other embodiments, a method is provided. The method includes receiving anatomic image data for an anatomic tree structure. The method further includes generating an initial segmentation of the anatomic image data. The initial segmentation includes a trunk structure and a branched structure unconnected to the trunk structure. The method further includes determining whether to connect the branched structure to the trunk structure based on an assessment of a shape of the branched structure and an assessment of a relationship between the trunk structure and the branched structure.

Consistent with other embodiments, a method is provided. The method includes receiving anatomic image data for an anatomic tree structure. The method further includes generating an initial segmentation of the anatomic image data. The initial segmentation includes a trunk structure and a branched structure unconnected to the trunk structure. The method further includes displaying the branched structure and the trunk structure on a display system. The branched structure is displayed with a visual characteristic different from the trunk structure. The method further includes receiving an indication of a user's intent to at least one of adding the branched structure to the trunk structure or removing the branched structure.

Consistent with other embodiments, a method is provided. The method includes receiving anatomic image data for an anatomic tree structure. The method further includes generating an initial segmentation of the anatomic image data. The initial segmentation includes a trunk structure and a branched structure unconnected to the trunk structure. The method further includes displaying the trunk structure on a display system. The method further includes receiving an indication of a user's intent to grow the initial segmentation into an indicated region adjacent to the trunk structure. The method further includes displaying the branched structure if the branched structure is located in the indicated region adjacent to the trunk structure.

Other embodiments include corresponding computer systems, apparatus, and computer programs recorded on one or more computer storage devices, each configured to perform the actions of the methods.

It is to be understood that both the foregoing general description and the following detailed description are exemplary and explanatory in nature and are intended to provide an understanding of the present disclosure without limiting the scope of the present disclosure. In that regard, additional

BRIEF DESCRIPTIONS OF THE DRAWINGS

FIG. 8A illustrates a simplified diagram of a medical instrument system according to some embodiments.

FIG. 8B illustrates a simplified diagram of a medical instrument with an extended medical tool according to some embodiments.

Figure 1A:
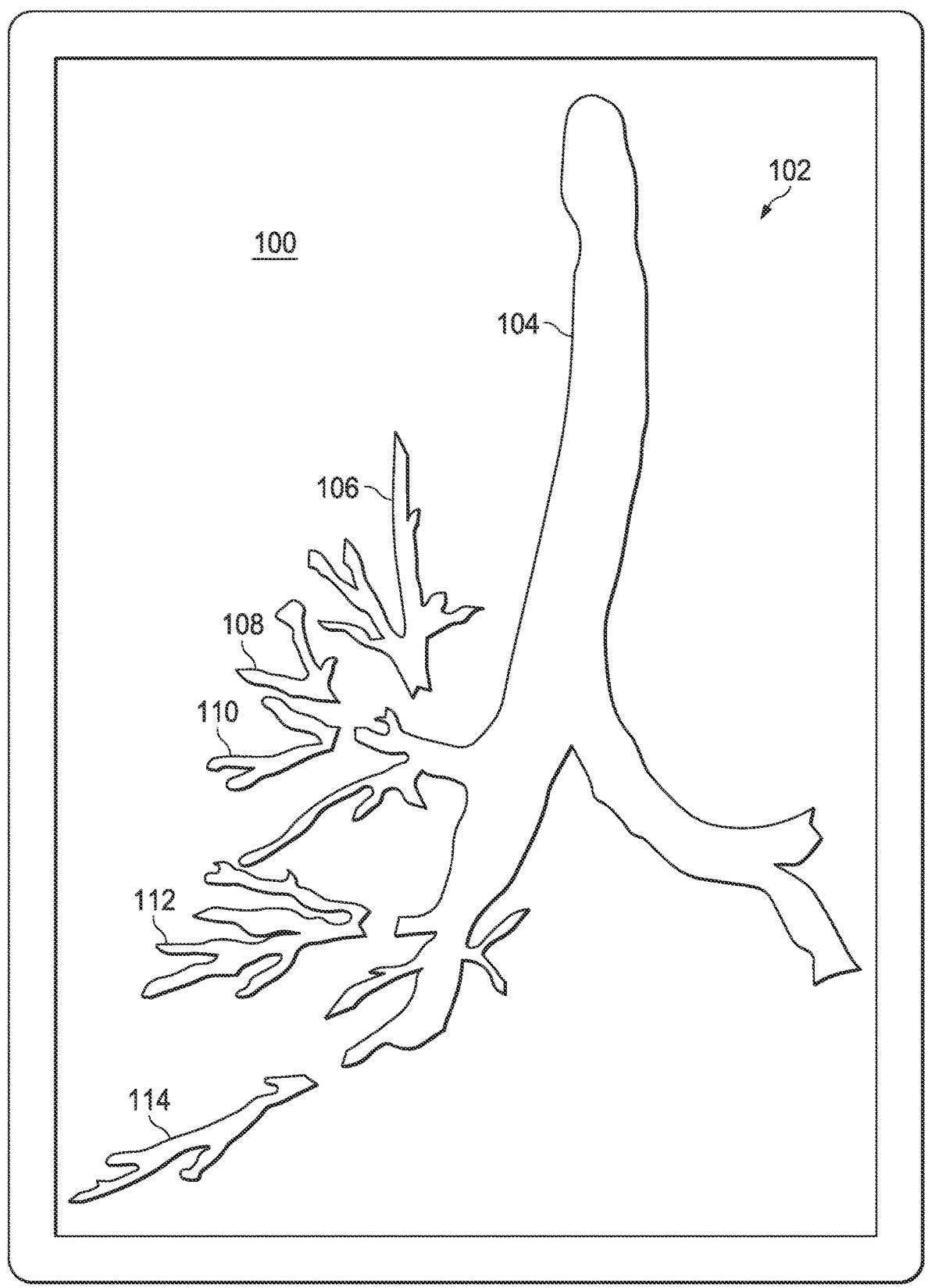
FIG. 1A illustrates a display including a segmented trunk structure and segmented branched structures unconnected to the trunk structure according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Various imaging techniques may be used to acquire anatomical image data of a patient anatomy for use in a variety of medical procedures including surgical, diagnostic, therapeutic procedures. For example, anatomical image data may be acquired using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Anatomical image data may be acquired preoperatively or intraoperatively. In some embodiments, anatomical image data may be used with a virtual visualization system to provide navigation assistance to an operator controlling a medical instrument during an image-guided surgical procedure.

Anatomical image data may be segmented to produce graphical units (e.g. pixels or voxels). Model-based or machine learning techniques may be used to associate a probability value with each graphical unit. The probability value may correspond to a type of anatomical tissue and thus may be used to differentiate tissues and generate segmented models of the anatomical tissue. If, for example, the anatomic structure is a lung, the probability value may correspond to soft tissue or to airways. Often, probability values alone provide only rudimentary information that may not be sufficient to generate an accurately segmented model of branched anatomical passageways, particularly when the anatomical image data set is noisy (e.g., inherent electronic noise, artifacts, or physical anomalies) or the passageways are very small. Thus, image data segmentation based on probability values alone may be insufficient to generate anatomical tree models that can be used in clinical applications. In the example of the lung, probability values may provide a false positive probability value for a graphical unit which may cause the graphical unit to be misclassified as an airway. Alternatively, the probability values may provide a false negative probability value for a graphical unit which may cause the graphical unit to be misclassified as not part of an airway. The systems and methods described below may be used to generate more accurate anatomical tree models (also referred to as anatomical branch models).

In some embodiments, an initial segmentation of anatomical image data of branched anatomical structures based on probability values may generate a tree model in which some branches (e.g., smaller or more distal branches) are separated or disconnected from the central structures or trunk of the model. The unconnected segmented structures may result from stenosis or passageway blockages that cause portions of passageways to be misclassified. FIG. 1A illustrates a display 100 of a tree model 102 including a segmented trunk structure 104 and segmented branched structures 106, 108, 110, 112, 114 unconnected to the trunk structure 104. The segmented trunk structure 104 and the segmented branched structures 106-114 are formed of segmented graphical units. In some embodiments, the segmented trunk structure 104 may include bifurcations resulting in branched structures, and in other embodiments the trunk structure may have no bifurcations and present as a generally elongated unidirectional structure. In some embodiments the unconnected branched structures 106-114 may include at least one bifurcation and at least two branched members. In alternative embodiments, the branched structures may include a single elongated branch member with no bifurcations.

Figure 1B:
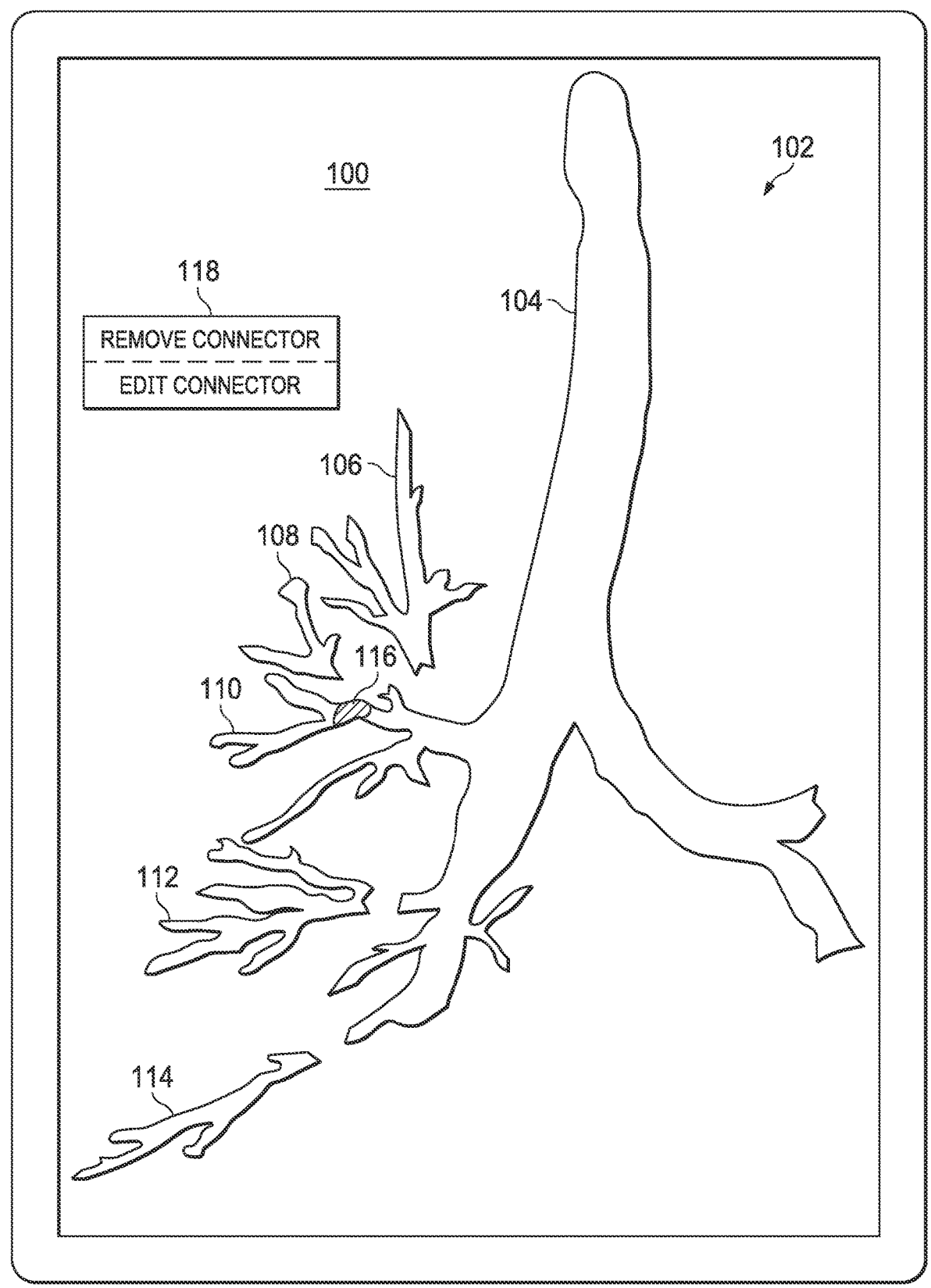
FIG. 1B illustrates a display including a segmented trunk structure, segmented branched structures unconnected to the trunk structure, and a connector structure connecting the segmented trunk structure to one of the segmented branched structures according to some embodiments.
Figure 2:
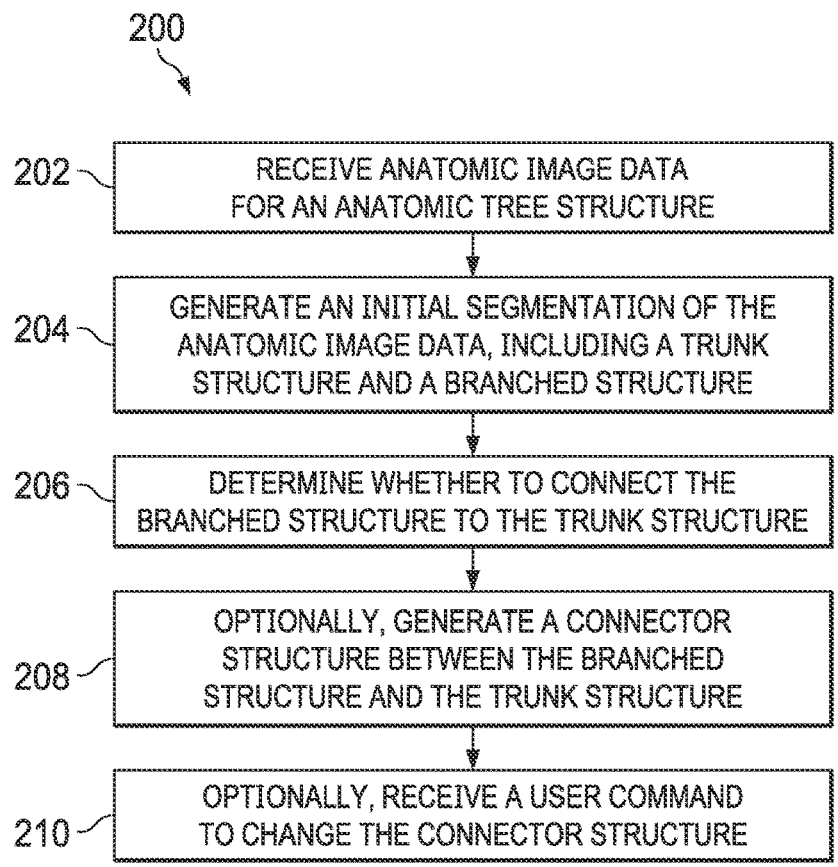
FIG. 2 illustrates a method for connecting segmented structures according to some embodiments.

FIG. 2 illustrates a method 200 for connecting one or more of the branched structures 106-114 to the trunk structure 104. The method 200 is illustrated as a set of operations or processes 202 through 210 and is described with continuing reference to FIGS. 1A and 1B. Not all of the illustrated processes 202 through 210 may be performed in all embodiments of method 200. Additionally, one or more processes that are not expressly illustrated in FIG. 2 may be included before, after, in between, or as part of the processes 202 through 210. In some embodiments, one or more of the processes 202 through 210 may be implemented, at least in part, in the form of executable code stored on non-transitory, tangible, machine-readable media that when run by one or more processors (e.g., the processors of control system) may cause the one or more processors to perform one or more of the processes. In one or more embodiments, the processes 202 through 210 may be performed by a control system.

At a process 202, anatomical image data for an anatomic tree structure is received. The anatomic tree structure may be any set of natural or surgically created connected passageways, in any of a variety of anatomic systems, including the colon, the intestines, the kidneys and kidney calices, the brain, the heart, the lungs, the circulatory system including vasculature, and/or the like. At a process 204, an initial segmentation of the anatomical image data is performed, resulting in the trunk structure 104 and the disconnected branched structures 106-114.

At a process 206, one of the branched structure 106-114 is evaluated to determine whether to connect the branched structure to the trunk structure 104. Determining whether a disconnected branched structure is a true structure of the tree model may be based on an assessment of one or more parameters including the shape of the branched structure and the relationship between the trunk structure and the branched structure. The assessment may consider the parameters relative to threshold values. For example, the branched structure may be required to have a shape with a threshold number of bifurcations or branched members. In one embodiment the shape of the branched structure must include a threshold value of one bifurcation and a threshold value of at least two branched members. The assessment may also consider the location and distance of the branched structure in relationship to the trunk structure. The assessment may also consider the size of the unconnected branched structure relative to a threshold value or relative to the trunk structure. The assessment may also consider the size of the unconnected branched structure in terms of the number to graphical units forming the branched structure. The assessment may also consider an orientation of the unconnected branched structure and/or the angle of the portion of the branched structure closest to the trunk structure. Matched angles of a connection portion of the trunk structure and at least one of the branched members of the branched structure may determine whether to select the branched structure for connection to the trunk structure. Any branched structure that meets or exceeds a threshold value for the selection parameter used may be connected to the trunk structure. Any branched structure that does not meet the threshold value for the selection parameter may be discarded and removed from display.

If, for example, the disconnected branched structure 110 is determined to be a branched structure that should be connected to the trunk structure 104 based on one or more of the assessed parameters, a control system may generate a plurality of graphical units forming a connector structure 116 (FIG. 1B) between the trunk and the branched structure 110. At optional process 208, a connector structure 116 is a tubular member generated between the branched structure 110 and the trunk structure 104. The size, shape, and orientation of the connector structure and the connection location on the trunk structure may be based on reference to the original anatomic image data and/or on the location and angle of the connection points on each of the connected structures. The connector structure 116 and the connected branched structure 110 may be displayed with a color, texture, transparency, outline or another visual characteristic distinguishable from the trunk structure.

In some embodiments, user interface components allow a user to undo system-generated connections between structures or alter the size, shape or connection points for the connector structures. At an optional process 210, a user command to change the connector structure 216 may be received via a user interface component such as menu 118. The menu 118 allows a user to, for example, select whether to remove the system generated connector structure 116 or edit some aspect of the connector structure 116 such as the location of the connector points or the thickness of the tube. In various embodiments, the user interface may be responsive to user input devices such as joysticks, trackballs, touchscreens, data gloves, trigger-guns, hand-operated controllers, voice recognition devices, eye-tracking devices, body motion or presence sensors, and/or the like. In various embodiments, all or fewer than all of the branched structures 106-114 may be evaluated for connection to the trunk structure. For example, if an anatomical target, such as a lesion or biopsy location, is located in a particular anatomic region, the unconnected branched structures near the target may be evaluated for connection but other unconnected branched structures in other areas may not be evaluated.

Figure 4:
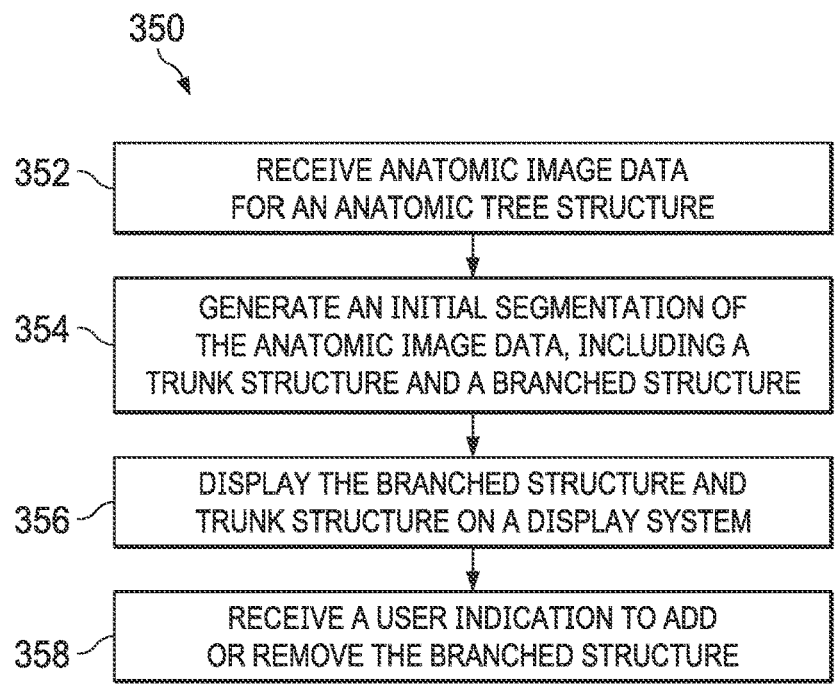
FIG. 4 illustrates a method for connecting segmented structures according to some embodiments.
Figure 3A:
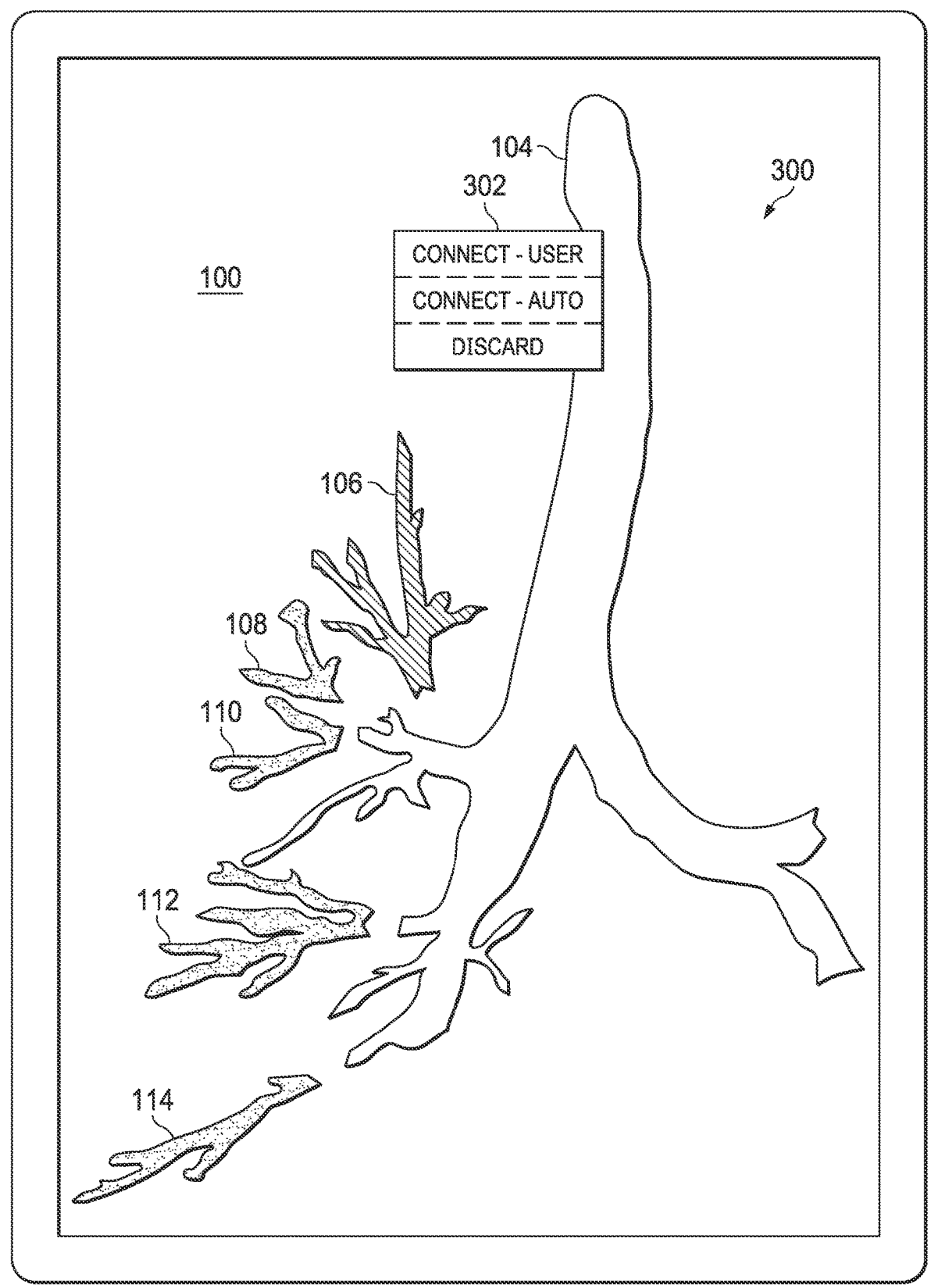
FIG. 3A illustrates a display including a segmented trunk structure, segmented branched structures unconnected to the trunk structure, and a user interface component for providing a user indication about one of the segmented branched structures according to some embodiments.
Figure 3B:
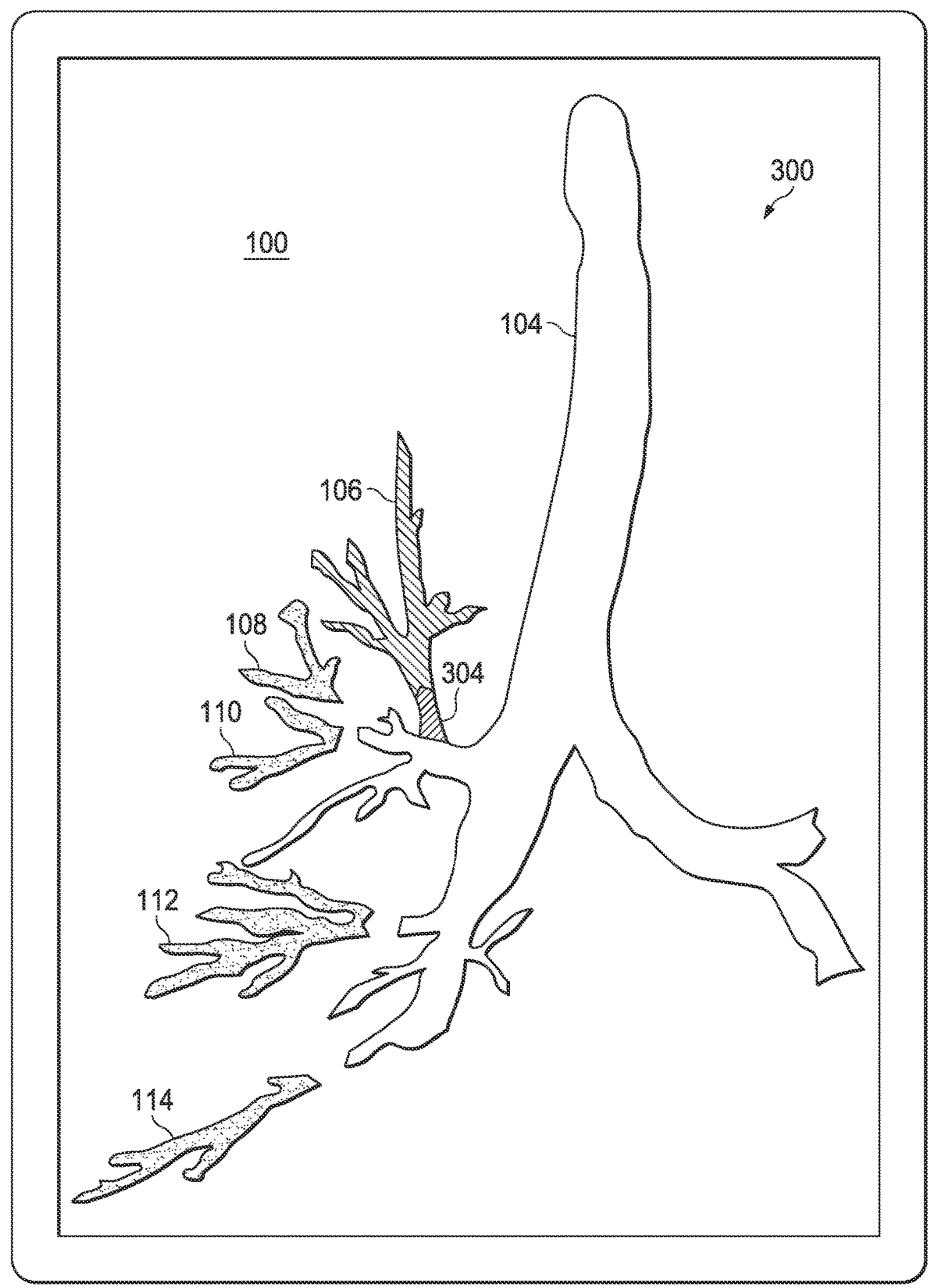
FIG. 3B illustrates a display including a segmented trunk structure, segmented branched structures unconnected to the trunk structure, and a connector structure connecting the segmented trunk structure to one of the segmented branched structures according to some embodiments.

In another embodiment, unconnected branched structures may be connected to the trunk structure based on a determination made by a user. FIG. 3A illustrates the display 100 with a tree model 300 including the segmented trunk structure 104 and the segmented branched structures 106, 108, 110, 112, 114 unconnected to the trunk structure 104. FIG. 4 illustrates a method 350 for connecting one or more of the branched structures 106-114 to the trunk structure 104. The method 350 is illustrated as a set of operations or processes and is described with continuing reference to FIGS. 3A and 3B. Not all of the illustrated processes may be performed in all embodiments of method 350. Additionally, one or more processes that are not expressly illustrated in FIG. 4 may be included before, after, in between, or as part of the processes described. In some embodiments, one or more of the processes may be implemented, at least in part, in the form of executable code stored on non-transitory, tangible, machine-readable media that when run by one or more processors (e.g., the processors of control system) may cause the one or more processors to perform one or more of the processes. In one or more embodiments, the processes may be performed by a control system.

At a process 352, anatomical image data for an anatomic tree structure is received. The process 352 may be substantially the same as process 202. At a process 354, an initial segmentation of the anatomical image data is performed, resulting in the trunk structure 104 and the disconnected branched structures 106-114. The process 354 may be substantially the same as process 204.

At a process 356, the unconnected branched structures 106-114 and the trunk structure 104 may be displayed on the display 100. In some embodiments, the unconnected branched structures 106-114 may be displayed with a color, texture, transparency, outline or another visual characteristic distinguishable from the trunk structure. One or more of the branched structures 106-114 may be evaluated by a user to determine whether the branched structure should be selected for connection to the trunk structure 104.

During the user evaluation, a selected branched structure under evaluation, e.g., structure 106 may be identified with a color, texture, transparency, outline or another visual characteristic distinguishable from the other branched structures 108-114. A user interface component, such as a menu 302 may be displayed for the selected structure 106 to allow the user to choose a disposition for the structure 106. For example, the user may select from menu options including a user-involved connector generation tool, an automatic connector generation tool, or a discard tool. At a process 358, an indication to add or discard the selected structure 106 is received from the user. For example, the user may choose an option from the menu 302.

If, for example, the user indicates that the disconnected branched structure 106 should be automatically connected to the trunk structure 104, a control system may generate a plurality of graphical units forming a connector structure 304 (FIG. 3B) between the trunk structure 104 and the branched structure 106. The connector structure 304 may be a tubular member generated between the branched structure 106 and the trunk structure 104. The size, shape, and orientation of the connector structure may be based on reference to the original anatomic image data and/or the location and angle of the connection points on each of the connected structures. If, for example, the user indicates that a manual process should be used (i.e., the user-involved connector generation tool) to connect the branched structure 106 to the trunk structure 104, the user may use a manual grow process to choose the size, shape, or other characteristics of the connector structure 304. The connector structure 304 and the connected branched structure 110 may be displayed with a color, texture, transparency, outline or another visual characteristic distinguishable from the trunk structure. If, for example the user indicates by menu selection that the disconnected branched structure 106 should be discarded, the branched structure 106 may be removed from the display.

Figure 5A:
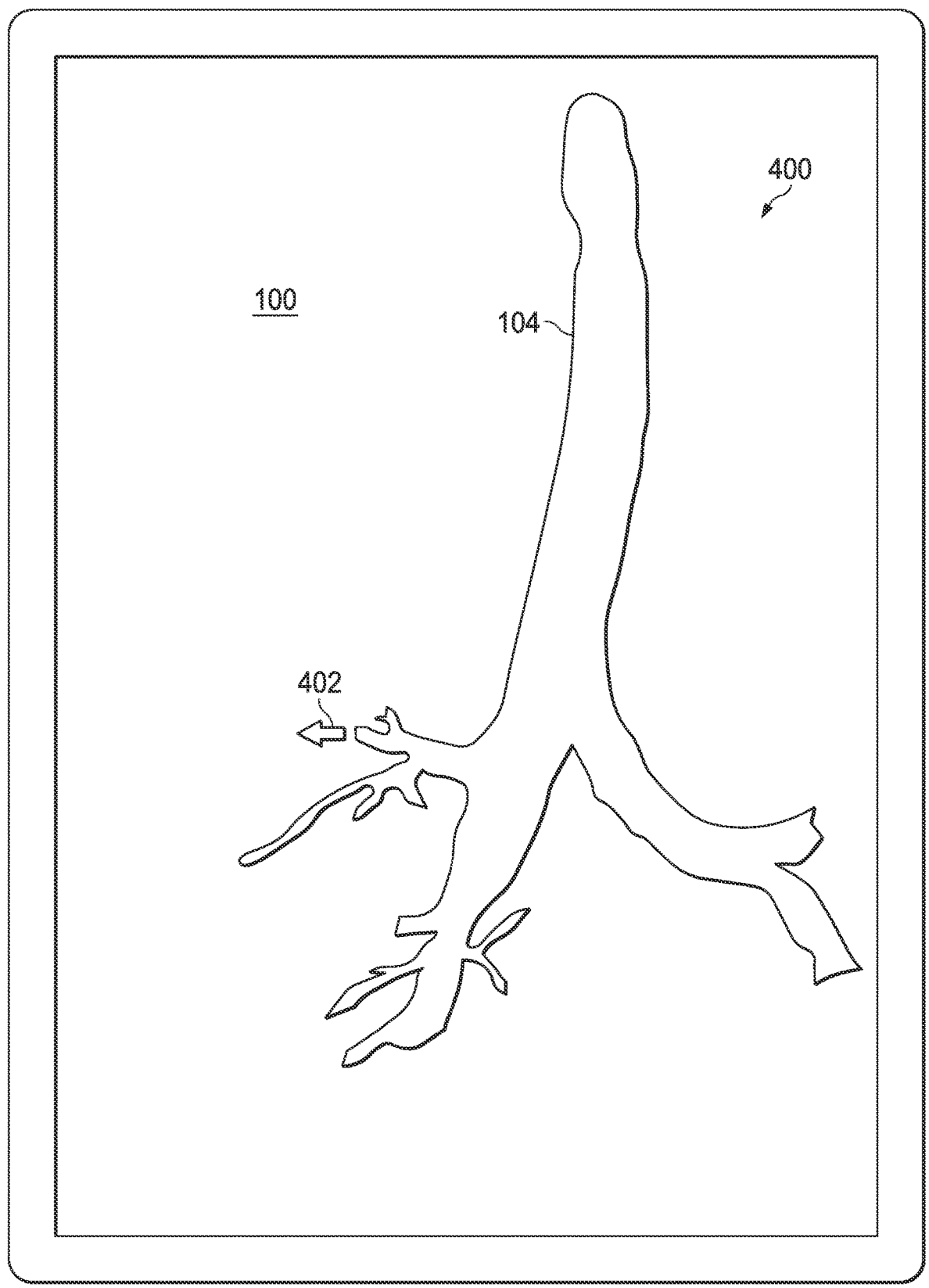
FIG. 5A illustrates a display including a segmented trunk structure and a user growth direction component according to some embodiments.
Figure 5B:
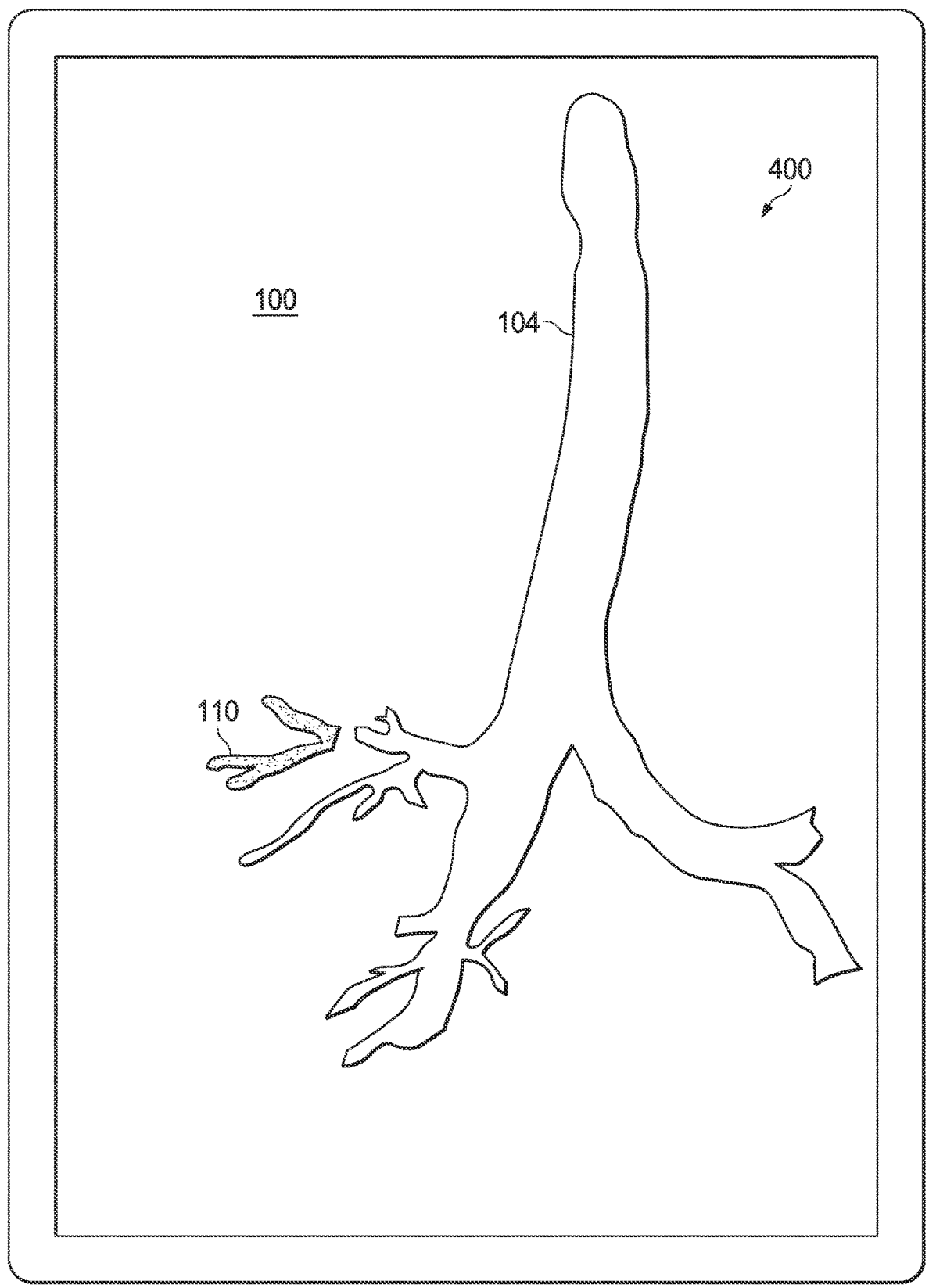
FIG. 5B illustrates a display including a segmented trunk structure and a segmented branched structure unconnected to the trunk structure according to some embodiments.
Figure 5C:
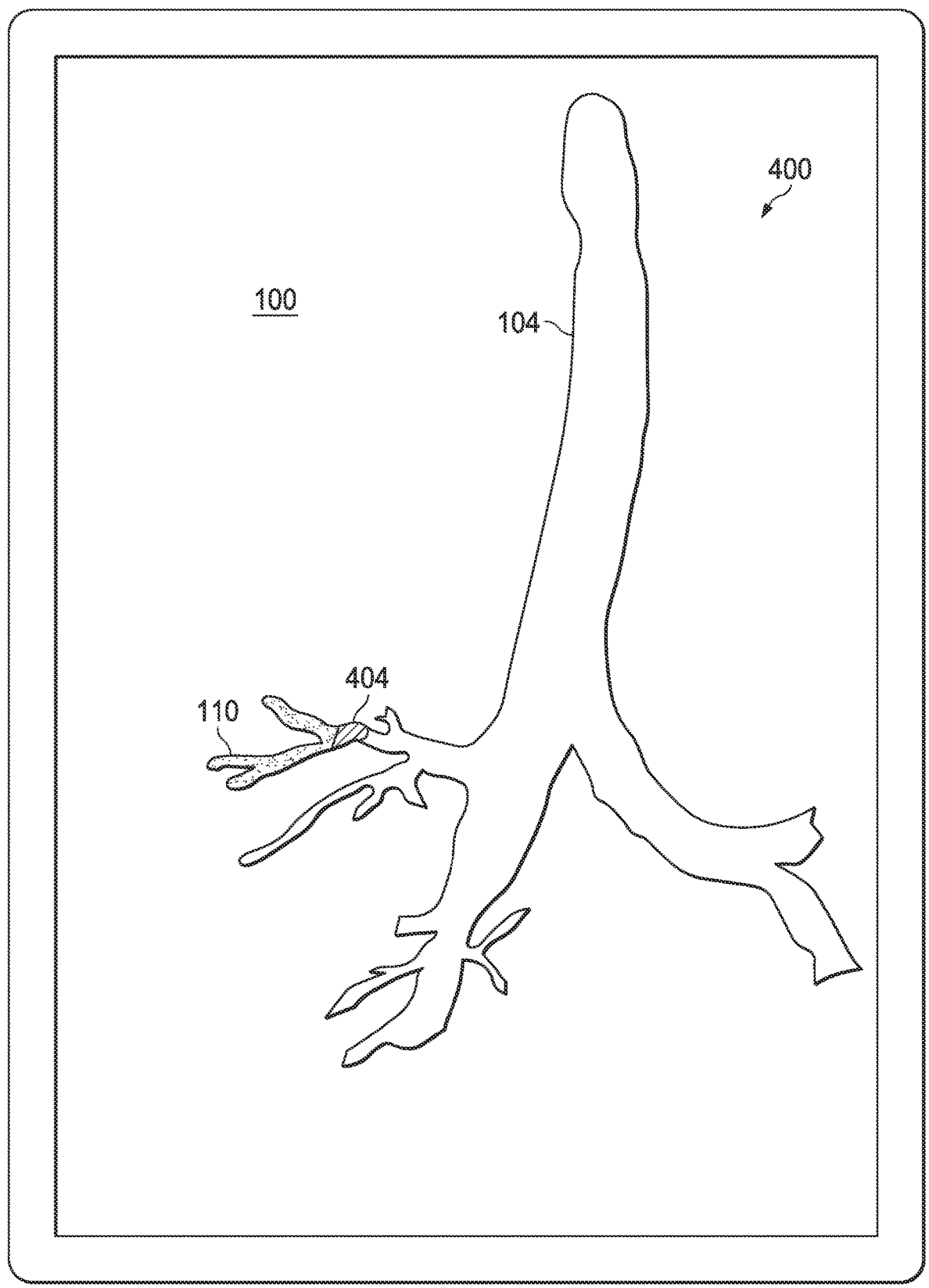
FIG. 5C illustrates a display including a segmented trunk structure, a segmented branched structure unconnected to the trunk structure, and a connector structure connecting the segmented trunk structure to one of the segmented branched structures according to some embodiments.
Figure 6:
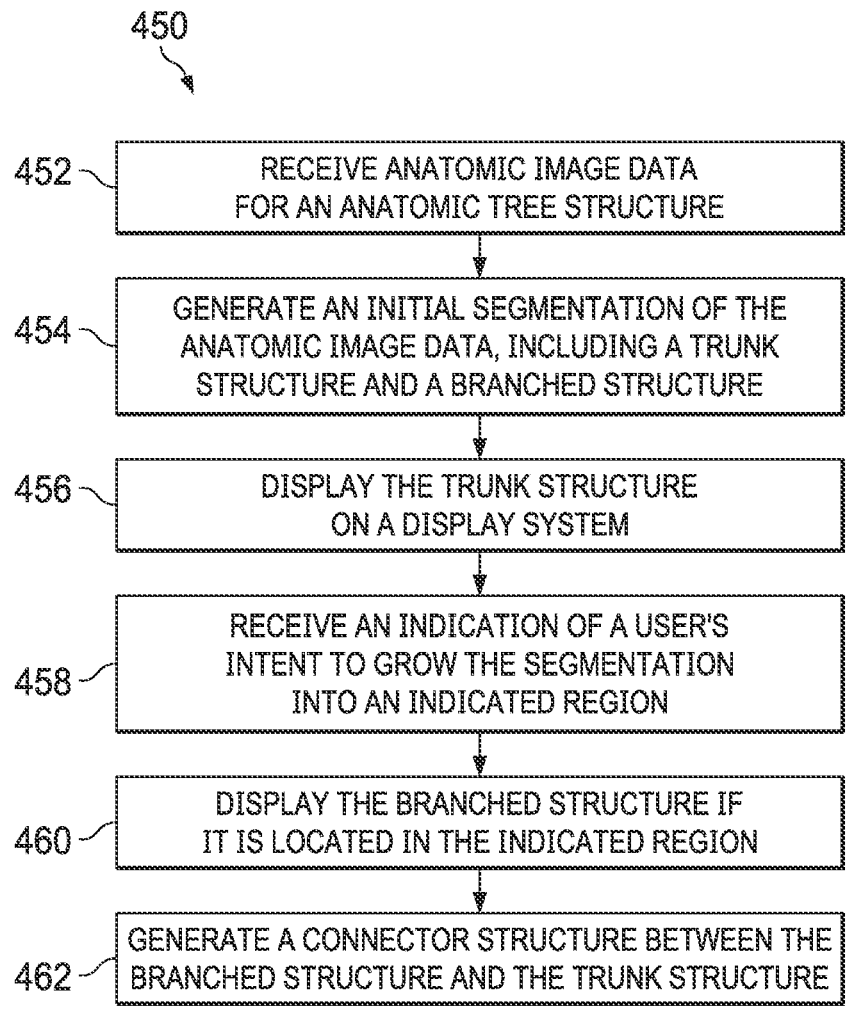
FIG. 6 illustrates a method for connecting segmented structures according to some embodiments.

In another embodiment, a user-driven segmentation growth process may reveal a disconnected branched structure for display when the user begins to grow the segmentation of the trunk structure (e.g., select graphical units to add to the trunk structure) into an area where the disconnected branched structures are located. FIG. 5A illustrates the display 100 with a tree model 400 including the segmented trunk structure 104. In this embodiment, display of the unconnected segmented branched structures 106, 108, 110, 112, 114 is suppressed and the unconnected branched structures are not visible on the display 100. FIG. 6 illustrates a method 450 for connecting one or more of the branched structures 106-114 to the trunk structure 104.

At a process 452, anatomical image data for an anatomic tree structure is received. The process 452 may be substantially the same as process 202. At a process 454, an initial segmentation of the anatomical image data is performed, resulting in the trunk structure 104 and the disconnected branched structures 106-114. The process 454 may be substantially the same as process 204.

At a process 456, the trunk structure 104 is displayed on the display system 100 as shown in FIG. 5A. The unconnected branched structures 106-114 are not displayed. To extend the trunk structure 104, the user may initiate a grow process to add graphical units to the trunk structure. At a process 458, an indication is received from the user selecting an area or region proximate to the trunk structure into which the user would like to grow the segmentation. As shown in FIG. 5A, an indication is received that the user intends to grow the segmentation of the trunk structure 104 in the direction of an area proximate to the trunk structure indicated by the arrow 402. At a process 460, the branched structure 110 located in the area indicated by the arrow 402 proximate to the trunk structure 104 is displayed. The remaining branched structures 106, 108, 112, 114 that are not in the indicated area proximate to the trunk structure 104 continue to not be displayed. At a process 462, a connector structure 404 is generated between the trunk structure 104 and the branched structure 110. Optionally, the processes 460 and 462 may be combined so that the uncovered branch structure 110 and the graphical units connecting the branched structure 110 to the trunk structure 104 may be displayed simultaneously when the area proximate to the trunk structure is indicated. In some embodiments, the connector structure 404 and the connected branched structure 110 may be displayed with a color, texture, transparency, outline or another visual characteristic distinguishable from the trunk structure. In some embodiments, the branched structures that are outside of areas selected by the user for growth of the segmentation are discarded and not included in the final segmented tree structure.

Figure 7:
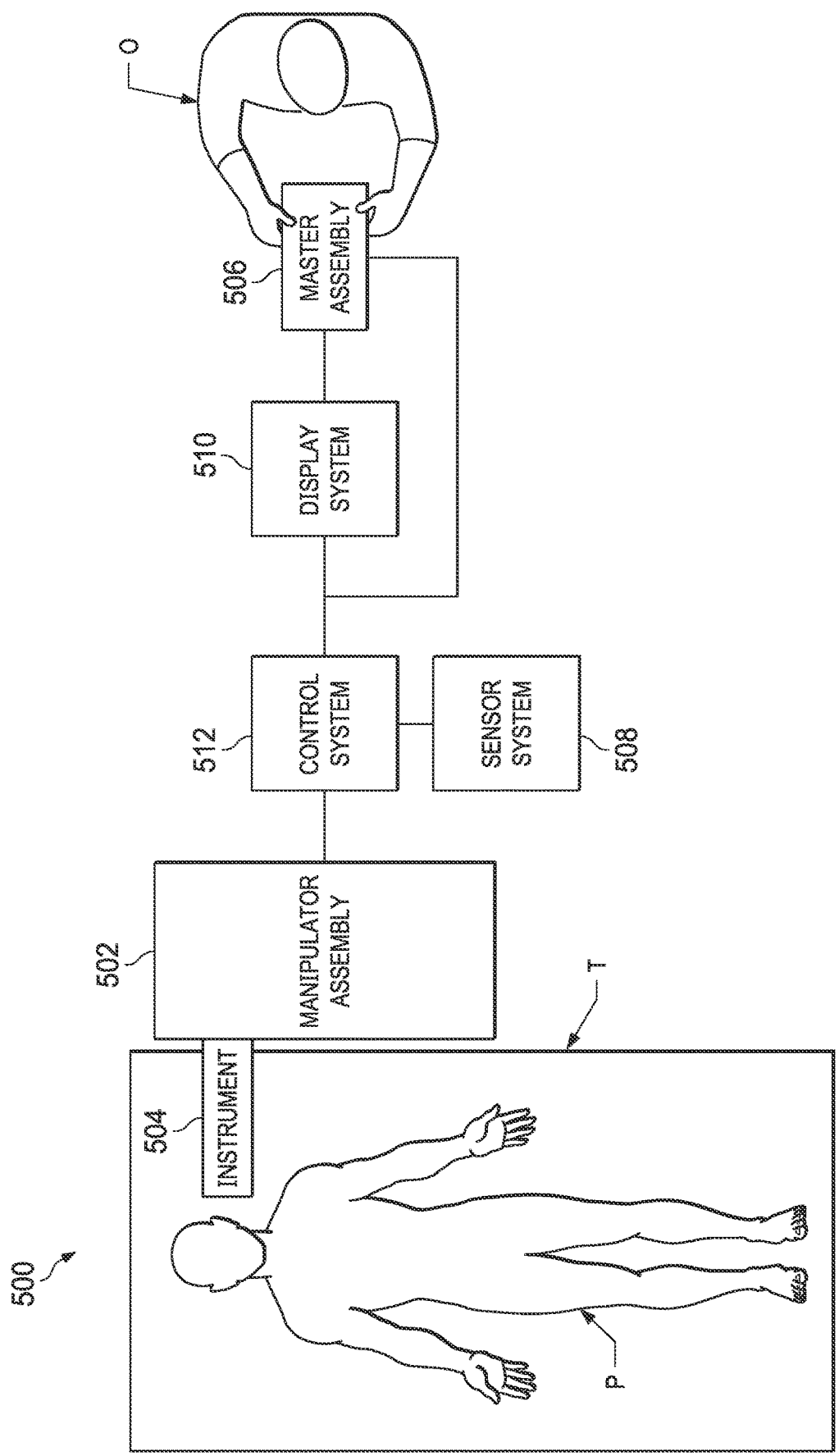
FIG. 7 illustrates a simplified diagram of a robotic or teleoperated medical system according to some embodiments.

In some embodiments, segmented tree structures may be used in an image-guided medical procedure performed with a teleoperated medical system as described in further detail below. While some embodiments are provided herein with respect to such procedures, any reference to medical or surgical instruments and medical or surgical methods is non-limiting. In some embodiments, the segmented tree structures may be used for non-teleoperational procedures involving guidance of traditional manually operated medical instruments. The systems, instruments, and methods described herein may be used for animals, human cadavers, animal cadavers, portions of human or animal anatomy, non-surgical diagnosis, as well as for industrial systems and general robotic, general teleoperational, or robotic medical systems. As shown in FIG. 7, medical system 500 generally includes a manipulator assembly 502 for operating a medical instrument 504 in performing various procedures on a patient P positioned on a table T. The manipulator assembly 502 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Master assembly 506 generally includes one or more control devices for controlling manipulator assembly 502. Manipulator assembly 502 supports medical instrument 504 and may optionally include a plurality of actuators or motors that drive inputs on medical instrument 504 in response to commands from a control system 512. The actuators may optionally include drive systems that when coupled to medical instrument 504 may advance medical instrument 504 into a naturally or surgically created anatomic orifice. Other drive systems may move the distal end of medical instrument 504 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 504 for grasping tissue in the jaws of a biopsy device and/or the like.

Teleoperated medical system 500 also includes a display system 510 for displaying an image or representation of the surgical site and medical instrument 504 generated by subsystems of sensor system 508. Display system 510 may include the display 100. Display system 510 and master assembly 506 may be oriented so operator O can control medical instrument 504 and master assembly 506 with the perception of telepresence.

In some embodiments, medical instrument 504 may include components of an imaging system, which may include an imaging scope assembly or imaging instrument that records a concurrent or real-time image of a surgical site and provides the image to the operator or operator O through one or more displays of medical system 500, such as one or more displays of display system 510. The concurrent image may be, for example, a two or three-dimensional image captured by an imaging instrument positioned within the surgical site. In some embodiments, the imaging system includes endoscopic imaging instrument components that may be integrally or removably coupled to medical instrument 504. However, in some embodiments, a separate endoscope, attached to a separate manipulator assembly may be used with medical instrument 504 to image the surgical site. The imaging system may be implemented as hardware, firmware, software or a combination thereof which interact with or are otherwise executed by one or more computer processors, which may include the processors of the control system 512.

Teleoperated medical system 500 may also include control system 512. Control system 512 includes at least one memory and at least one computer processor (not shown) for effecting control between medical instrument 504, master assembly 506, sensor system 508, and display system 510. Control system 512 also includes programmed instructions (e.g., a non-transitory machine-readable medium storing the instructions) to implement some or all of the methods described in accordance with aspects disclosed herein, including instructions for providing information to display system 510.

Control system 512 may optionally further include a virtual visualization system to provide navigation assistance to operator O when controlling medical instrument 504 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

FIG. 8A is a simplified diagram of a medical instrument system 600 according to some embodiments. Medical instrument system 600 includes elongate device 602, such as a flexible catheter, coupled to a drive unit 604. Elongate device 602 includes a flexible body 616 having proximal end 617 and distal end or tip portion 618. Medical instrument system 600 further includes a tracking system 630 for determining the position, orientation, speed, velocity, pose, and/or shape of distal end 618 and/or of one or more segments 624 along flexible body 616 using one or more sensors and/or imaging devices as described in further detail below.

Tracking system 630 may optionally track distal end 618 and/or one or more of the segments 624 using a shape sensor 622. Shape sensor 622 may optionally include an optical fiber aligned with flexible body 616 (e.g., provided within an interior channel (not shown) or mounted externally). The optical fiber of shape sensor 622 forms a fiber optic bend sensor for determining the shape of flexible body 616. In one alternative, optical fibers including Fiber Bragg Gratings (FBGs) are used to provide strain measurements in structures in one or more dimensions. In some embodiments, tracking system 630 may optionally and/or additionally track distal end 618 using a position sensor system 620. Position sensor system 620 may be a component of an EM sensor system with position sensor system 520 including one or more conductive coils that may be subjected to an externally generated electromagnetic field.

Flexible body 616 includes a channel 621 sized and shaped to receive a medical instrument 626. FIG. 8B is a simplified diagram of flexible body 616 with medical instrument 626 extended according to some embodiments. In some embodiments, medical instrument 626 may be used for procedures such as surgery, biopsy, ablation, illumination, irrigation, or suction. Medical instrument 626 can be deployed through channel 621 of flexible body 616 and used at a target location within the anatomy. Medical instrument 626 may include, for example, image capture probes, biopsy instruments, laser ablation fibers, and/or other surgical, diagnostic, or therapeutic tools. Medical instrument 626 may be used with an imaging instrument (e.g., an image capture probe) also within flexible body 616. Medical instrument 626 may be advanced from the opening of channel 621 to perform the procedure and then retracted back into the channel when the procedure is complete. Medical instrument 626 may be removed from proximal end 617 of flexible body 616 or from another optional instrument port (not shown) along flexible body 616.

Flexible body 616 may also house cables, linkages, or other steering controls (not shown) that extend between drive unit 604 and distal end 618 to controllably bend distal end 618 as shown, for example, by broken dashed line depictions 619 of distal end 618. In some examples, at least four cables are used to provide independent "up-down" steering to control a pitch of distal end 618 and "left-right" steering to control a yaw of distal end 618.

The information from tracking system 630 may be sent to a navigation system 632 where it is combined with information from image processing system 631 and/or the preoperatively obtained models to provide the operator with real-time position information. In some examples, the real-time position information may be displayed on display system 510 of FIG. 7 for use in the control of medical instrument system 600. In some examples, control system 512 of FIG. 7 may utilize the position information as feedback for positioning medical instrument system 600.

In some examples, medical instrument system 600 may be teleoperated within medical system 500 of FIG. 7. In some embodiments, manipulator assembly 502 of FIG. 7 may be replaced by direct operator control. In some examples, the direct operator control may include various handles and operator interfaces for hand-held operation of the instrument.

One or more elements in embodiments of this disclosure may be implemented in software to execute on a processor of a computer system such as control processing system.

When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth, IrDA, HomeRF, IEEE 802.11, DECT, and Wireless Telemetry.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

In some instances well known methods, procedures, components, and circuits have not been described in detail so as not to unnecessarily obscure aspects of the embodiments. This disclosure describes various instruments, portions of instruments, and anatomic structures in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
a display system; and
a control system communicatively coupled to the display system, the control system configured to:
receive anatomic image data for an anatomic tree structure;
generate an initial segmentation of the anatomic image data, the initial segmentation including a trunk structure and a branched structure unconnected to the trunk structure;
display the unconnected branched structure and the trunk structure on the display system, wherein the branched structure is displayed with a visual characteristic different from the trunk structure;
provide a menu associated with the branched structure on the display system; and
receive an indication of a user's intent to at least one of add the branched structure to the trunk structure or remove the branched structure from the display system, wherein the indication of the user's intent is received via a choice selected from the menu.

2. The system of claim 1 wherein the visual characteristic is a color different from the trunk structure.

3. The system of claim 1 wherein the visual characteristic is a transparency different from the trunk structure.

4. The system of claim 1 wherein if an indication of a user's intent to add the branched structure to the trunk structure is received, the control system is further configured to:
determine a set of connection locations and generate a connector structure between the trunk structure and the branched structure between the connection locations.

5. The system of claim 4 wherein generating the connector structure includes referencing the anatomic image data to determine a dimension of the connector structure.

6. The system of claim 1 wherein if the indication of a user's intent to remove the branched structure is received, the control system is further configured to:
remove the branched structure from the display system.

7. A method performed by a control system communicatively coupled to a display system, comprising:
receiving anatomic image data for an anatomic tree structure;
generating an initial segmentation of the anatomic image data, the initial segmentation including a trunk structure and a branched structure unconnected to the trunk structure;
displaying the unconnected branched structure and the trunk structure on the display system, wherein the branched structure is displayed with a visual characteristic different from the trunk structure;
providing a menu associated with the branched structure on the display system; and
receiving an indication of a user's intent to at least one of add the branched structure to the trunk structure or remove the branched structure from the display system, wherein the indication of the user's intent is received via a choice from the menu.

8. The method of claim 7 wherein the visual characteristic is a color different from the trunk structure.

9. The method of claim 7 wherein the visual characteristic is a transparency different from the trunk structure.

10. The method of claim 7 wherein if an indication of a user's intent to add the branched structure to the trunk structure is received, the method further comprises:

determining a set of connection locations and generating a connector structure between the trunk structure and the branched structure between the connection locations.

11. The method of claim 10 wherein generating the connector structure includes referencing the anatomic image data to determine a dimension of the connector structure.

12. The method of claim 7 wherein if the indication of a user's intent to remove the branched structure is received, the method further comprises:
removing the branched structure from the display system.

13. A non-transitory machine-readable media storing instructions that, when executed by one or more processors of a control system, cause the one or more processors to:
receive anatomic image data for an anatomic tree structure;
generate an initial segmentation of the anatomic image data, the initial segmentation including a trunk structure and a branched structure unconnected to the trunk structure;
display the unconnected branched structure and the trunk structure on a display system communicatively coupled to the control system, wherein the branched structure is displayed with a visual characteristic different from the trunk structure;
providing a menu associated with the branched structure on the display system; and
receive an indication of a user's intent to at least one of add the branched structure to the trunk structure or remove the branched structure from the display system, wherein the indication of the user's intent is received via a choice selected from the menu.

14. The non-transitory machine-readable media of claim 13 wherein the visual characteristic is a color different from the trunk structure.

15. The non-transitory machine-readable media of claim 13 wherein the visual characteristic is a transparency different from the trunk structure.

16. The non-transitory machine-readable media of claim 13 further storing instructions that, when executed by the one or more processors, cause the one or more processors to:
determine a set of connection locations when an indication of a user's intent to add the branched structure to the trunk structure is received; and
generate a connector structure between the trunk structure and the branched structure between the connection locations.

17. The non-transitory machine-readable media of claim 13 further storing instructions that, when executed by the one or more processors, cause the one or more processors to:
remove the branched structure from the display system when the indication of a user's intent to remove the branched structure is received.

* * * * *